US005095160A

United States Patent [19]

Penella et al.

[11] Patent Number: 5,095,160
[45] Date of Patent: Mar. 10, 1992

[54] CONVERSION OF BENZENE TO TOLUENE

[75] Inventors: Filippo Penella; Marvin M. Johnson, both of Bartlesville, Okla.

[73] Assignee: Phillips Petroleum Company, Bartlesville, Okla.

[21] Appl. No.: 719,899

[22] Filed: Jun. 24, 1991

[51] Int. Cl.[5] ............................ C07C 2/24; C07C 6/00
[52] U.S. Cl. ..................................... 585/476; 585/266; 502/325
[58] Field of Search ........................ 585/476, 475, 266

[56] References Cited

U.S. PATENT DOCUMENTS

| | | | |
|---|---|---|---|
| 2,404,498 | 7/1946 | Ipatieff et al. | 585/404 |
| 3,668,264 | 6/1972 | Alley | 585/404 |
| 4,329,531 | 5/1982 | Murtha et al. | 585/268 |
| 4,409,412 | 10/1983 | Haag et al. | 585/454 |
| 4,447,554 | 5/1984 | Murtha et al. | 502/73 |
| 4,926,000 | 5/1990 | Morrison | 585/476 |

OTHER PUBLICATIONS

Ipatieff et al, Jour. Amer. Chem. Soc. 69, 710, 1947.
Journal of the American Chemical Society, vol. 69, 1947, p. 710; article by V. N. Ipatieff et al.
Industrial and Engineering Chemistry, vol. 40, No. 11, Nov. 1948, pp. 2059-2062; article by V. N. Ipatieff et al.

*Primary Examiner*—Asok Pal
*Assistant Examiner*—P. Achutamurthy
*Attorney, Agent, or Firm*—K. K. Brandes

[57] ABSTRACT

Benzene is converted to toluene in the presence of free hydrogen and a supported nickel metal catalyst.

8 Claims, No Drawings

CONVERSION OF BENZENE TO TOLUENE

BACKGROUND OF THE INVENTION

This invention relates to the catalytic conversion of benzene to toluene, essentially in the absence of an added methylation agent.

The catalytic self-alkylation of benzene to toluene, essentially in the absence of methane as alkylation agent, is known and has been described in The Journal of the American Chemical Society, Volume 69, 1947, page 710. However, this prior art process requires high reaction pressures (over 200 atm.). The present invention provides an improved process for converting benzene to toluene, at commercially more feasible reaction conditions, in particular at relatively low pressures. Conversion of benzene to toluene is commercially important because benzene is carcinogenic, whereas toluene is not.

SUMMARY OF THE INVENTION

It is an object of this invention to convert benzene to toluene, essentially in the absence of an added alkylating agent (such as methane). It is another object of this invention to provide a catalytic process for converting benzene to toluene, at relatively low reaction pressures. Other objects and advantages become apparent from the detailed disclosure and the appended claims.

In accordance with this invention, a gaseous feed which comprises (preferably consists essentially of) benzene and free hydrogen is contacted in a reaction zone with a catalyst comprising nickel metal and an inorganic refractory support material (preferably alumina), essentially in the absence of added methane, under such conditions as to at least partially convert benzene to toluene.

DETAILED DESCRIPTION OF THIS INVENTION

Any feed which contains benzene can be used in the process of this invention. The feed may be liquid or gaseous. When a liquid feed is used, it will be vaporized before it enters the catalytic reaction zone. The feed can be substantially pure benzene or it can be diluted with inert substances, such as $N_2$ or He. The feed is essentially free of methane. A non-limiting example of a feed is one obtained by stripping benzene impurities from wastewater with nitrogen gas. Other feeds can be derived from processes for removal of benzene from fuels such as gasoline. The benzene content in the feed can range from about 0.5 to about 100 percent by volume, and preferably is about 90-100 volume-%.

Hydrogen gas can be introduced into the reactor premixed with the benzene-containing feed. Or hydrogen gas can be introduced separately, but concurrently with the benzene containing feed. Hydrogen gas can be provided as essentially pure hydrogen gas or in admixture with an inert diluent, such as $N_2$, He and the like. Any effective molar ratio of hydrogen to benzene can be employed in the reaction zone. The molar ratio of $H_2$ to benzene generally is in the range of about 1:20 to about 1:1, and preferably is in the range of about 1:10 to about 1:2.

Any effective supported nickel catalyst can be employed in the reaction zone. The nickel content of the catalyst generally is in the range of about 5 to about 70 weight-% Ni, and preferably is in the range of about 15 to about 60 weight-% Ni. The nickel component of the catalyst consists essentially of metallic Ni and is supported by an inorganic carrier material. Any suitable inorganic support material can be employed. Non-limiting examples of such support materials are alumina, aluminum phosphate, silica, titania ($TiO_2$), zirconia ($ZrO_2$), hafnia ($HfO_2$), zinc oxide, zinc aluminate ($ZnAl_2O_4$), aluminates of alkaline earth metals (i.e., Be, Mg, Ca, Sr, Ba), zinc titanate ($Zn_2TiO_4$), titanates of alkaline earth metals, and mixtures of two or more than two of the above compounds. The presently preferred support material is alumina.

The supported nickel catalysts which are effective in the process of this invention are either commercially available or can be prepared by persons skilled in the art, preferably by impregnating the support material with a dissolved nickel compound (such as Ni acetate), followed by heating to about 230°-260° C. and subsequently reducing treatment with molecular hydrogen at about 350°-450° C. The surface area (determined by the BET method employing $N_2$) of the catalyst generally is in the range of about 100 to about 400 m$^2$/g, and the catalyst particle size generally is in the range of about 1 to about 10 mm.

The benzene and hydrogen containing mixture entering the catalytic reaction zone can be contacted with the supported nickel catalyst in any suitable manner, at any suitable reaction conditions which are effective to convert at least a portion of benzene to toluene. This process can be carried out continuously or as a batch process. Preferably, the benzene and hydrogen containing gaseous feed is continuously passed over a layer of the catalyst or through a fixed bed of the catalyst in a suitable reactor (such as a tubular steel vessel). Hydrogen gas and benzene feed can be introduced into the reactor separately, but concurrently, or premixed. If $H_2$ and benzene streams are separately introduced into the reactor, means for mixing the two streams before they enter the reaction zone containing the catalyst should preferably be provided, such as static (baffle-type) mixing means.

Preferred reaction (contacting) conditions in the reaction zone include a temperature in the range of about 350° F. (177° C.) to about 750° F. (399° C.), preferably 500°-700° F. (260°-371° C.); a reaction pressure in the range of about 0 psig (atmospheric pressure) to about 500 psig (about 35 atm), preferably about 30-200 psig (about 2-14 atm); a reaction time in the range of about 0.5 minute to about 60 minutes preferably about 1-10 minutes; a liquid hourly space velocity of benzene in the range of about 0.01 to about 20 volume benzene per volume catalyst per hour (generally expressed as cc/cc/hr at 25° C./1 atm), preferably about 0.5-5 cc/cc/hr; and a gas hourly space velocity of $H_2$ (at 25° C./1 atm) in the range of about 30 to about 3,000 cc/cc/hr, preferably about 100-1,000 cc/cc/hr.

The product which exits from the reaction vessel comprises unconverted benzene, unconverted $H_2$, formed toluene, methane and minor amounts of other formed substances (such as n-hexane, cyclohexane, methylcyclopentane, methylcyclohexane, biphenyl, naphthalene). Toluene, the desired material, can be separated from unconverted benzene and $H_2$ and by-products by any suitable means (e.g., fractionation, extractive distillation, adsorption/desorption, and the like). Unconverted feed materials (i.e., benzene and $H_2$) can be recycled to the reactor. Recovered toluene can be used in any suitable application (such as an additive to gasoline).

The following examples are presented to further illustrate the process of this invention and are not to be construed as unduly limiting the scope of this invention.

EXAMPLE I

This example illustrates the effect of free hydrogen on the "self-alkylation" of benzene to toluene, in the presence of a supported nickel catalyst. A 10 cc (8.82 g) sample of a commercial 20–40 mesh catalyst containing 56 weight-% Ni on mixed refractory oxides (commercially available as "Harshaw Ni-3285" from Engelhard Corporation, Menlo Park, Edison, N.J.) was placed on top of a layer of glass beads in a ½ inch tubular stainless steel reactor. A second layer of glass beads was placed on top of the fixed bed of the supported nickel catalyst.

The reactor was heated to the desired reaction temperature (500°–625° F.; measured in the center of the catalyst bed) while $H_2$ was passed through the reactor at a rate of 40 cc/minute. Then the flow of $H_2$ was stopped, the reactor was flushed with $N_2$ gas, and liquid benzene was pumped (in a down-flow direction) into the reactor, at a liquid hourly space velocity (LHSV) of 3 cc benzene per cc catalyst per hour, while a pressure of 50 psig was maintained at the reaction temperature. In control runs, $N_2$ gas was co-fed (with benzene) at a rate of 50 cc/minute, while in invention runs, $H_2$ gas was co-fed (with benzene) at a rate of 50 cc/minute. The reactor effluent was cooled to room temperature and the condensed product was analyzed by means of a gas chromatograph. Test results are summarized in Table I.

TABLE I

| Run | Time on Stream (Hours) | Gas Co-Feed | Temp. (°F.) | Benzene | Toluene | Others[1] |
|---|---|---|---|---|---|---|
| 1 | 1 | Nitrogen | 600 | 98.9 | 0.7 | 0.4 |
|   | 2 | " | 600 | 98.9 | 0.7 | 0.4 |
|   | 3 | " | 600 | 99.0 | 0.6 | 0.4 |
|   | 3.5 | Hydrogen | 600 | 92.8 | 6.6 | 0.6 |
|   | 4.5 | " | 625 | 91.7 | 7.5 | 0.8 |
| 2 | 1 | Nitrogen | 591 | 98.5 | 1.1 | 0.4 |
|   | 2 | " | 592 | 98.8 | 0.9 | 0.3 |
|   | 3 | " | 599 | 98.9 | 0.8 | 0.3 |
|   | 4 | " | 600 | 98.9 | 0.8 | 0.3 |
|   | 4.5 | Hydrogen | 619 | 93.1 | 6.1 | 0.8 |
|   | 5 | " | 615 | 93.7 | 5.7 | 0.6 |
|   | 6 | " | 615 | 94.1 | 5.3 | 0.6 |
|   | 7 | " | 615 | 94.1 | 5.3 | 0.6 |
| 3 | 1 | Hydrogen | 622 | 91.6 | 7.5 | 0.8 |
|   | 2 | " | 624 | 91.1 | 7.9 | 1.0 |
|   | 3 | " | 624 | 90.4 | 8.5 | 1.2 |
|   | 4 | " | 624 | 92.8 | 6.3 | 0.9 |
|   | 5 | " | 624 | 93.4 | 5.8 | 0.8 |
|   | 6.3 | " | 625 | 93.0 | 6.2 | 0.8 |
| 4 | 1 | Nitrogen | 504 | 99.5 | 0.3 | 0.1 |
|   | 2 | $H_2 + N_2$[2] | 537 | 97.8 | 1.1 | 0.8 |
|   | 3 | " | 540 | 96.4 | 2.1 | 1.2 |
|   | 3.5 | " | 580 | 93.7 | 3.5 | 2.2 |

[1] includes cyclohexane, alkylbenzenes other than toluene, methylcyclohexane, methylcyclopentane, n-hexane, biphenyl and naphthalene.
[2] a mixture of $H_2$ and $N_2$ was used at a $H_2/N_2$ volume rate of 1:2 to 2:1.

Test data in Table I clearly show that, at comparable reaction temperatures, considerably more benzene was converted to toluene when $H_2$ was present during the reaction.

EXAMPLE II

This example illustrates the use of a Ni/alumina catalyst in the "self-alkylation" of benzene to toluene in the presence of free hydrogen.

A $Ni/Al_2O_3$ catalyst containing 18 weight-% Ni was prepared as follows. 20 grams (26.5 cc) of 20–40 mesh alumina (having a surface area of 230 $m^2/g$ and a pore volume of 0.59 cc/g; commercially available as "Harshaw ALX-526A-20" from Engelhard Corporation, Edison, N.J.) were dried for 1.5 hours at 110° C. To the dried alumina sample, which weighed 18.8 g, was added a solution of 9.0 g $Ni(CH_3CO_2)_2 \bullet 4H_2O$ (available from Mallinckrodt, Inc., St. Louis, Mo.) in 15 cc methanol. The resulting mixture was dried for 1 hour at 110° C., and then calcined in a muffle furnace at 230°–260° C. for 4 hours (so as to decompose the Ni acetate to Ni oxide). The calcined catalyst was impregnated again with a Ni acetate solution containing 8.25 g $Ni(CH_3CO_2)_2 \bullet 4H_2O$ in 15 cc methanol, dried at 110° C., and calcined at 230°–260° C. for 3 hours. The resulting catalyst material was sieved through a 40 mesh size screen, and 22.7 g of a 20–40 mesh grayish-black material was recovered.

The above-described catalyst material was reduced in hydrogen gas at 750° F. (400° C.) for 5 hours, and was then employed in the conversion of benzene to toluene, substantially in accordance with the procedure described in Example I. Test results are summarized in Table II.

TABLE II

| Run | Time on Stream (Hours) | Gas Co-Feed | Pressure (psig) | Temp. (°F.) | Benzene | Toluene | Others |
|---|---|---|---|---|---|---|---|
| 5 | 1 | $H_2$ | 50 | 627 | 88.9 | 9.8 | 1.3 |
|   | 1.5 | " | " | 626 | 89.1 | 9.6 | 1.3 |
|   | 3 | " | " | 622 | 89.5 | 9.1 | 1.4 |
|   | 5 | " | " | 622 | 90.1 | 8.5 | 1.4 |
|   | 7 | " | " | 622 | 91.0 | 7.8 | 1.2 |
| 6 | 1 | $N_2$ | 50 | 604 | 99.0 | 0.6 | 0.4 |
|   | 2 | " | " | 604 | 99.4 | 0.3 | 0.3 |
|   | 4 | " | " | 604 | 99.4 | 0.3 | 0.3 |
|   | 4.5 | $H_2$ | 50 | 621 | 89.1 | 10.0 | 0.9 |
|   | 5.1 | " | " | 621 | 90.0 | 9.2 | 0.8 |
|   | 7 | " | " | 622 | 90.8 | 8.4 | 0.8 |
|   | 9 | " | " | 622 | 90.8 | 8.4 | 0.8 |
| 7 | 1 | $N_2$ | 0 | 607 | 99.6 | 0.2 | 0.2 |
|   | 2 | " | " | 607 | 99.7 | 0.2 | 0.1 |
|   | 2.5 | $H_2$ | " | 614 | 94.2 | 5.5 | 0.3 |
|   | 3 | " | " | 613 | 93.0 | 6.7 | 0.3 |
|   | 4 | " | " | 612 | 93.7 | 6.0 | 0.3 |
|   | 5.5 | " | " | 608 | 94.6 | 5.1 | 0.3 |
|   | 7.0 | " | 50 | 614 | 90.3 | 8.9 | 0.8 |
|   | 8.2 | " | " | 611 | 90.5 | 8.8 | 0.7 |

Test results summarized in Table II confirm the beneficial effect of hydrogen on the yield of toluene. Furthermore, test data for run 7 indicate that an increase in pressure resulted in a higher toluene yield.

Reasonable variations and modifications can be made within the scope of the disclosure and the appended claims without departing from the scope of the invention.

That which is claimed is:

1. A process for converting benzene to toluene which comprises the steps of:
    contacting a feed mixture comprising benzene and free hydrogen and containing essentially no methane with a catalyst composition consisting essentially of (a) nickel metal and (b) an inorganic support material selected from the group consisting of alumina, aluminum phosphate, silica, titania, zirconia, hafnia, zinc oxide, zinc aluminate, aluminates of alkaline earth metals, zinc titanate, titanates of alkaline earth metals and mixtures thereof, at a reaction temperature in the range of about 500° to about 700° F. and a reaction pressure in the range of about 0 to about 500 psig, under such reaction conditions as to obtain a toluene-containing reaction product; and recovering toluene from said toluene-containing reaction product.

2. A process in accordance with claim 1, wherein the molar ratio of free hydrogen to benzene is in the range of about 1:20 to about 1:1.

3. A process in accordance with claim 2, wherein said molar ratio is in the range of about 1:10 to about 1:2.

4. A process in accordance with claim 1, wherein said catalyst composition contains about 5–70 weight-% nickel metal.

5. A process in accordance with claim 1, wherein said inorganic support material is alumina.

6. A process in accordance with claim 1, wherein the nickel metal content in said catalyst composition is about 5–70 weight-% and said inorganic support material is alumina.

7. A process in accordance with claim 1, wherein said reaction pressure is about 30–200 psig.

8. A process in accordance with claim 1, wherein said reaction conditions further comprises a reaction time of about 0.5 minute to about 60 minutes.

* * * * *

UNITED STATES PATENT AND TRADEMARK OFFICE
CERTIFICATE OF CORRECTION

PATENT NO.   :   5,095,160
DATED        :   March 10, 1992
INVENTOR(S)  :   Filippo Pennella and Marvin M. Johnson It is certified that error appears in the above-identified patent and that said Letters Patent is hereby corrected as shown below:

Title page, item (75), delete "Penella" and insert therefor

--- Pennella ---.

Signed and Sealed this

Twenty-second Day of June, 1993

Attest:

MICHAEL K. KIRK

*Attesting Officer*      Acting Commissioner of Patents and Trademarks